US012544174B2

(12) United States Patent
Aljuboori

(10) Patent No.: US 12,544,174 B2
(45) Date of Patent: Feb. 10, 2026

(54) LEVELING DRAPE FOR ENDOVASCULAR PROCEDURES

(71) Applicant: Zaid Aljuboori, Wilkes Barre, PA (US)

(72) Inventor: Zaid Aljuboori, Wilkes Barre, PA (US)

( * ) Notice: Subject to any disclaimer, the term of this patent is extended or adjusted under 35 U.S.C. 154(b) by 50 days.

(21) Appl. No.: 18/741,081

(22) Filed: Jun. 12, 2024

(65) Prior Publication Data

US 2024/0423744 A1 Dec. 26, 2024

Related U.S. Application Data

(60) Provisional application No. 63/521,931, filed on Jun. 20, 2023.

(51) Int. Cl.

*A61B 46/23* (2016.01)
*A61B 46/20* (2016.01)
*A61G 13/12* (2006.01)

(52) U.S. Cl.

CPC .......... *A61B 46/23* (2016.02); *A61G 13/1245* (2013.01); *A61G 13/1265* (2013.01); *A61B 2046/201* (2016.02); *A61G 2210/50* (2013.01)

(58) Field of Classification Search

CPC . A61G 13/1245; A61G 13/1265; A61F 5/012; A61F 5/30; A61B 46/00; A61B 46/27; A61B 5/02233; A61B 17/12; A61B 17/132; A61B 17/135; A61B 46/30

See application file for complete search history.

(56) References Cited

U.S. PATENT DOCUMENTS

2005/0126577 A1* 6/2005 Griesbach .............. A61B 46/00 128/849
2016/0008072 A1* 1/2016 Pecora ................... A61B 46/27 128/853

FOREIGN PATENT DOCUMENTS

EP 2387965 A2 * 11/2011 ............. A61B 46/30

* cited by examiner

*Primary Examiner* — Ophelia A Hawthorne
(74) *Attorney, Agent, or Firm* — Boyle Fredrickson, S.C.

(57) ABSTRACT

A sterile surgical drape includes left and right inflatable supports leveling the upper surface of the drape to better corral instruments during angiographic procedures. An optional center inflatable support helps center the drape and provides a continuation of this work surface. Multiple sealable openings can be provided at common groin and wrist locations.

11 Claims, 3 Drawing Sheets

LEVELING DRAPE FOR ENDOVASCULAR PROCEDURES

CROSS REFERENCE TO RELATED APPLICATION

This application claims the benefit of U.S. provisional application 63/521,931 filed Jun. 20, 2023 and hereby incorporated by reference.

STATEMENT REGARDING FEDERALLY SPONSORED RESEARCH OR DEVELOPMENT

--

BACKGROUND OF THE INVENTION

The present invention relates generally to surgical drapes used to establish a sterile field during surgery and, in particular, to a surgical drape providing an improved work surface.

Angiographic and similar procedures employ catheters, wires, tubes, and syringes for the introduction of contrast media, stents, balloons, and the like into the patient during radiographic imaging. Such equipment can be long (~80-300 cm) to enable the operator to reach distant vessels in the human body. During these procedures, the patient will typically be supine on a horizontal surgical table and the patient may be covered by a surgical drape establishing a sterile operating field. The drape may be "fenestrated" to provide a hole through the drape at the access site. In some cases, the edges of the opening may be attached to the patient's skin with an adhesive.

A surgical drape is typically sized to extend over the patient as well as the left and right edges of the table presenting a generally upwardly smooth convex surface which will increase the likelihood of equipment positioned in the vicinity of the patient's legs falling to the floor and becoming contaminated. Damaged or contaminated equipment can result in increased procedure costs according to the price of the equipment which can range between 500-20,000 dollars. Contaminated equipment creates an increased risk of infection and replacing such equipment after damage or contamination can introduce significant delays in time critical procedures as new catheters or the like are prepared for insertion into the patient.

SUMMARY OF THE INVENTION

The present invention provides a surgical drape having inflatable lateral supports to equipment and devices against falling to the floor. The inflatable supports may be shaped and positioned to provide centering and retention of the drape on the patient and to position precut openings at locations of the groin or wrists being common access sites for angiographic procedures.

In one embodiment, the invention provides a surgical drape having sterile sheet sized to cover an area of a patient when lying in a horizontal position on a table, the sheet having left and right edges extending laterally beyond a left and right side of the patient. A first and second inflatable chamber is attached under the left and right edges and are sized to elevate the left and right edges above the table when inflated.

It is thus a feature of at least one embodiment of the invention to provide an improved working surface on the surgical drape that is more closely level.

The first and second inflatable chamber may have an inflated height of at least 4 inches between the lower surface adapted to contact the table when inflated and an upper surface defining a height of the left and right edge, respectively.

It is thus a feature of at least one embodiment of the invention to provide positive support of the left and right edges of the drape by the table.

The first and second inflatable chambers may present an upwardly concave surface to the sterile sheet when positioned flanking the legs of an average sized adult and inflated.

It is thus a feature of at least one embodiment of the invention to provide a surface that tends to corral material on the surgical drape.

The sheet may be sized to cover a superior portion of the patient above the groin region and an inferior portion of the patient below the groin region and the first and second inflatable chambers may be limited to the second inferior portion.

It is thus a feature of at least one embodiment of the invention to provide a surgical drape that can cover a substantial portion of the patient without interference between the inflatable chambers and the patient's arms.

The sterile drape may further include a third inflatable chamber positioned between the first and second inflatable chambers and sized to be positioned between the legs of the patient.

It is thus a feature of at least one embodiment of the invention to provide a more nearly level surface over a larger area when the patient's legs are separated.

The first, second, and third inflatable chambers may include an interconnecting pressure-equalization channel and/or may provide separate inflation valves.

It is thus a feature of at least one embodiment of the invention to allow flexible inflation of a subset of the chambers or simultaneous inflation of all chambers as desired.

The sterile polymer sheet may provide at least two openings positioned at at least one of a patient groin area and patient wrist area, the openings having releasable covers.

It is thus a feature of at least one embodiment of the invention to provide a drape particularly suited for angiographic procedures where wrist or groin access is required.

The left and right edges may extend beyond the first and second inflatable chamber to provide a downwardly extending drape section when positioned on the patient on a radiographic table.

It is thus a feature of at least one embodiment of the invention to provide a drape that fully covers the patient table and patient near the area of access.

The downwardly extending drape section may provide an upwardly open pouch.

It is thus a feature of at least one embodiment of the invention to provide a storage or capture area accessible to the healthcare professional during use of the drape.

These particular objects and advantages may apply to only some embodiments falling within the claims and thus do not define the scope of the invention.

DETAILED DESCRIPTION OF THE PREFERRED EMBODIMENT

Figure 1:
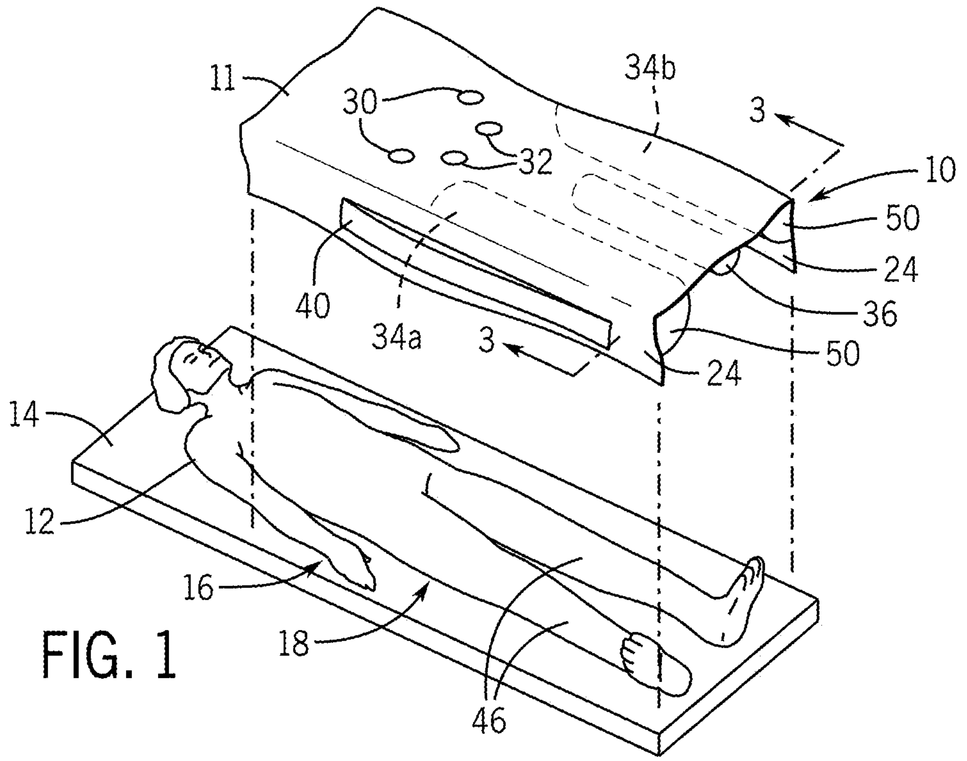
FIG. 1 is an exploded perspective view showing a patient in a supine position on a surgical table as may be covered by a surgical drape according to the present invention and showing the positioning of inflatable supports, openings, and side pockets of the surgical drape.
Figure 2:
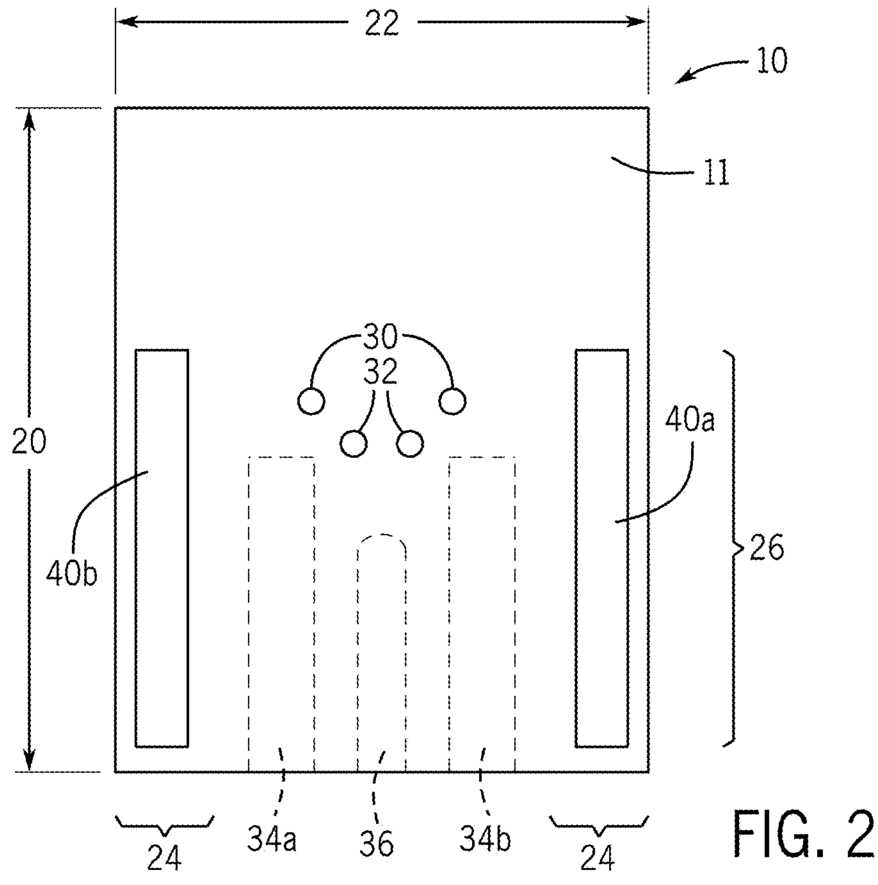
FIG. 2 is a top plan view of the surgical drape of FIG. 1 in a flattened configuration showing the relative location of the attachment of the inflatable supports, openings, and side pockets.

Referring now to FIGS. 1 and 2, a surgical drape 10, according to the present invention, is adapted to be placed on a patient 12 supported in a lying (supine or prone) position on a horizontal patient table 14, for example, for an angiographic procedure. The surgical drape 10 may include a drape material 11 constructed of a thin flexible sheet material which may naturally drape over the patient. The drape material 11 may be a woven or nonwoven material such as that commercially available from 3M under the trade name Biocade™.

In one nonlimiting example, all or a center of the drape material 11 may be laminated from four layers including a first layer being a high-density polyethylene film having a thickness of approximately five mils with small apertures to allow fluids to flow to an absorbent layer underneath while blocking lint from the absorbent layer from reaching the patient. This layer may be blue in color to absorb light from the overhead lamps and reduces glare for the doctor and comport with traditional trade coloring. This layer may be high-density polyethylene, 4.8 mils. thick, and weighs 13.6 grams per square meter. The second layer is an absorbent nonwoven white, unembossed air laid fabric composed of bleached virgin wood pulp fibers and bonded with a latex binder made by "fiberizing" cellulose (wood) pulp in a series of hammemills. The fiberized pulp is then blown onto a wire screen running through an air laid machine. Each side of the web may be sprayed with a binder to hold the fibers in sheet form. This layer may be approximately 70 mils. thick and is intended to absorb liquid. The third layer is a polyethylene film whose main function is to act as a barrier for fluid leakage to the patient and is 2 mils. thick. The final layer may be a print-bonded polyester laminated to the bottom side of the drape and acts as a comfort layer between the patient and the polyethylene film. The layers may be laminated together by a water-based adhesive.

In one embodiment, the surgical drape 10 is sized to cover a wrist region 16 and groin region 18 of the patient and may, for example, extend from the patient's shoulders to the patient's in for a patient of average size. In one nonlimiting example, the surgical drape 10 may have an inferior-superior length 20 of 130 inches (or greater than 77 inches) and a lateral width 22 of 90 inches (or greater than 30 inches). Importantly, the drape is sized to have a lateral width 22 greater than the width of the patient table 14 (for example, greater than 26 inches) so as to have a skirt portion 24 that will drape down below the patient table 14 during use, for example, by a distance greater than 6 inches.

Referring still to FIGS. 1 and 2, and inferior portion 26 of the surgical drape 10 may provide for a left and right wrist opening 30 through the drape material 11 and may be positioned at the wrist regions 16 of the patient's wrist during use for an average patient. Similarly, the surgical drape 10 may provide and left and right groin openings 32 at the groin region 18 during use for an average patient.

Positioned inferiorly to the left and right wrist openings 30 so as to be free from interference with the patient's hands are a left and right inflatable chamber 34*a* and 34*b* extending in a generally inferior-superior direction to flank and be outside of the patient's right and left leg (as depicted) during use. Positioned slightly below the groin openings 32 and centered between the left and right inflatable chambers 34 is a central inflatable chamber 36 that may fit between the patient's legs 46 when the surgical drape 10 is properly positioned and also extend parallel to the patient's superior-inferior axis. These inflatable chambers 34 and 36 may be constructed of a flexible polymer material that is airtight and may be adhered or welded to the drape material 11 or may be formed in part from the drape material 11 for its constituent layers. Generally, each of the inflatable chambers 34 and 36 may provide a generally superior-inferiorly extending tube leading to flexible end panels 50, the latter enforcing the desired cross-sectional shape of the chambers 34 and 36. Internal gusseting may also be provided to control the cross-sectional shape as desired.

Patch pockets 40*a* and 40*b* may be attached to outer surfaces of the skirt portions 24 to open upwardly when the skirt portions 24 are draped downwardly over the edges of the table 14. The patch pockets 40 may extend in an inferior-superior direction by more than 20 inches to regions above and below the groin region 18 and wrist regions 16 and may have a height of at least 6 inches. Generally, the patch pockets 40 will be fluid resistant to retain liquids and materials inserted therein. In some embodiments, the patch pockets 40 may include a drain valve at their lowest extent (not shown) to enable them to be connected to suction tubing to remove blood and or fluid accumulated during the procedure that could pull laterally on the surgical drapes 10.

Figure 3:
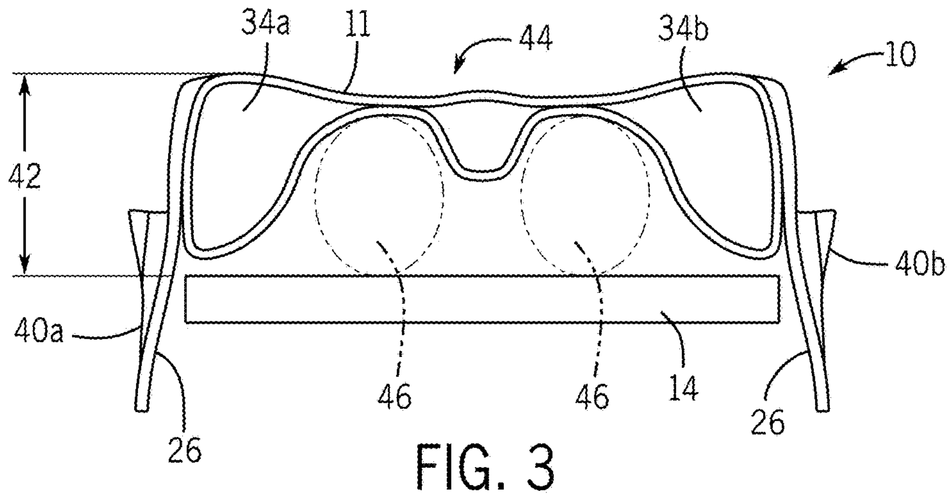
FIG. 3 is a cross-sectional view along line 3-3 of FIG. 1 showing the positioning of the inflatable supports about a patient's legs.

Referring now to FIG. 3, the inflatable chambers 34*a* and 34*b* are sized to have a height 42 when inflated to support the surgical drape 10 above the table 14 and, impart, a slightly concave shape to an upper work surface 44 provided by the surgical drape 10 over the table 14 and extending from the left to the right side of the table 14 when the surgical drape 10 is positioned on an average sized patient. This concave work surface 44 may provide improved retention of surgical instruments such as catheters, syringes, and the like.

For this purpose, a lower edge of the inflatable chambers 34 may contact an upper surface of the left and right edges of the table 14 to the left and right of the patient's legs 46 providing positive support of the work surface 44. Alternatively, inflatable chambers 34 may provide a buttress against the outer surfaces of the patient's legs 46 supporting the work surface 48 in cantilever. In the former case the height of the inflatable chamber 34 may be at least four inches and preferably greater than five inches between an upper surface of the table 14 and the work surface 44.

The inflatable chambers 34*a* and 34*b* will generally have an increasing height as one moves from a medial to a lateral position thus providing an angular lower surface that offers a self-centering of the surgical drape 10. Similarly, the central inflatable chamber 36 may be downwardly convex to be self-centered between the patient's legs and to provide appropriate spacing between the patient's legs 46. The central inflatable chamber 36 may be sized to descend to contact the table 14 or (as depicted) may operate in a truss fashion to provide a support of the drape material 11 between the patient's legs supported by the patient's legs.

Figure 4:
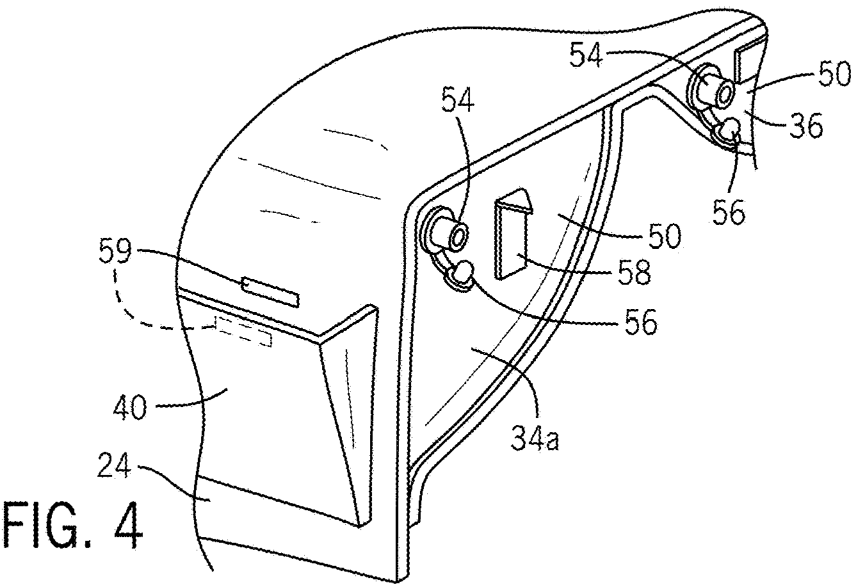
FIG. 4 is a perspective fragmentary view of an inferior end of the surgical drapes showing inflation valves, the side pockets, and a deflation tab.

Referring now to FIG. 4, the end panels 50 of the inferior ends of the inflatable chambers 34*a*, and 34*b* and 36 may each provide inflation valves 54 of conventional design including an internal one-way flapper valve (not shown) and a closure cap 56 to close the inflation valve 54 after inflation. The inflation valves 44 allow the surgical drape 10 to be shipped uninflated and then inflated prior to use. An optional tear-off tab 58 may be provided to allow rapid deflation of the inflatable chambers 34 and 36 upon completion of the surgical procedure prior to compacting and disposal of the surgical drape 10.

The upper openings of the patch pockets 40 may provide for adhesive or hook and loop closure fasteners 59 to allow them to be releasably secured in a closed position during or after use.

Figure 5:
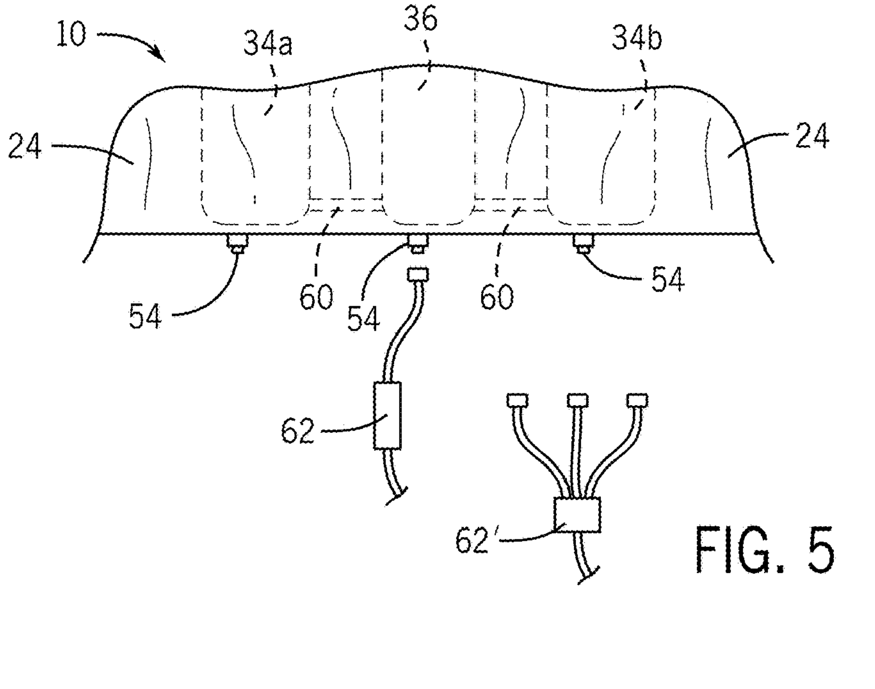
FIG. 5 is a top plan view of the surgical drape of FIG. 1 showing optional pressure-equalization channels allowing the inflation of the channels individually or in tandem.

Referring now to FIG. 5, an internal pressure equalization channel 60 may be provided between the inflatable chamber 36 and each of the inflatable chambers 34*a* and 34*b* to allow simultaneous inflation of all chambers from a single inflation hose 62 and single inflation valve 54, for example, connecting with a pump or source of pressurized air and providing a pressure limiting regulator. Alternatively, a multi-hose inflation fixture 62' may be provided connecting simultaneously to multiple inflation valves of 54 for similar purpose. The internal pressure equalization channel 60 may also be eliminated or blocked to allow selective inflation of particular inflatable chambers 34 or 36 for different procedures.

Figure 6:
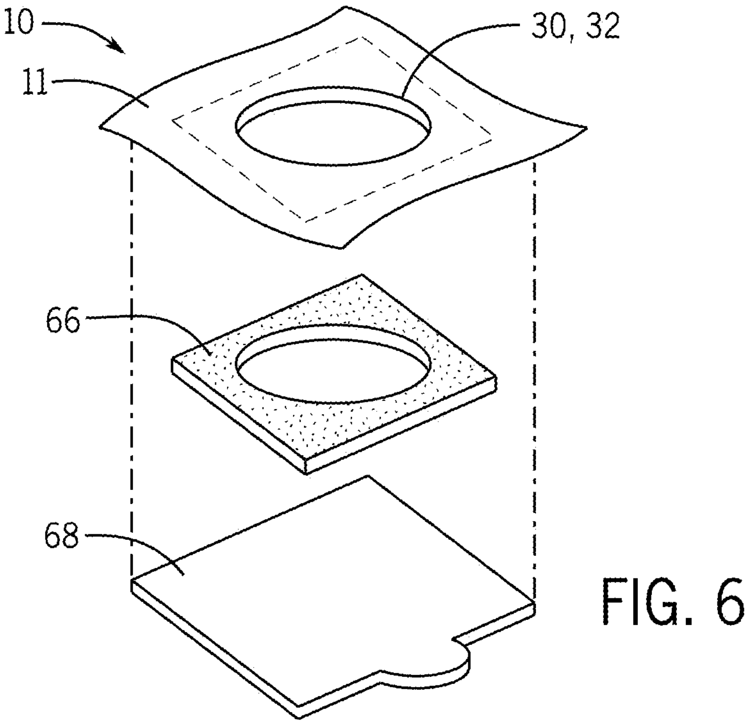
FIG. 6 is an exploded fragmentary view of an opening in the surgical drape showing an adhesive sealing member positioned beneath the opening to cover the opening when not in use or to expose an adhesive when the opening is in use.

Referring now to FIG. 6, the wrist openings or groin openings 30 or 32 may include an underlying adhesive layer 66 in turn covered by a blocking release liner 68. Particular openings 30 or 32 that are not used are left closed by the release liner which may be removed for openings that are used to expose the adhesive of the adhesive layer 66 to attach the drape material 11 to the patient's skin.

Figure 7:
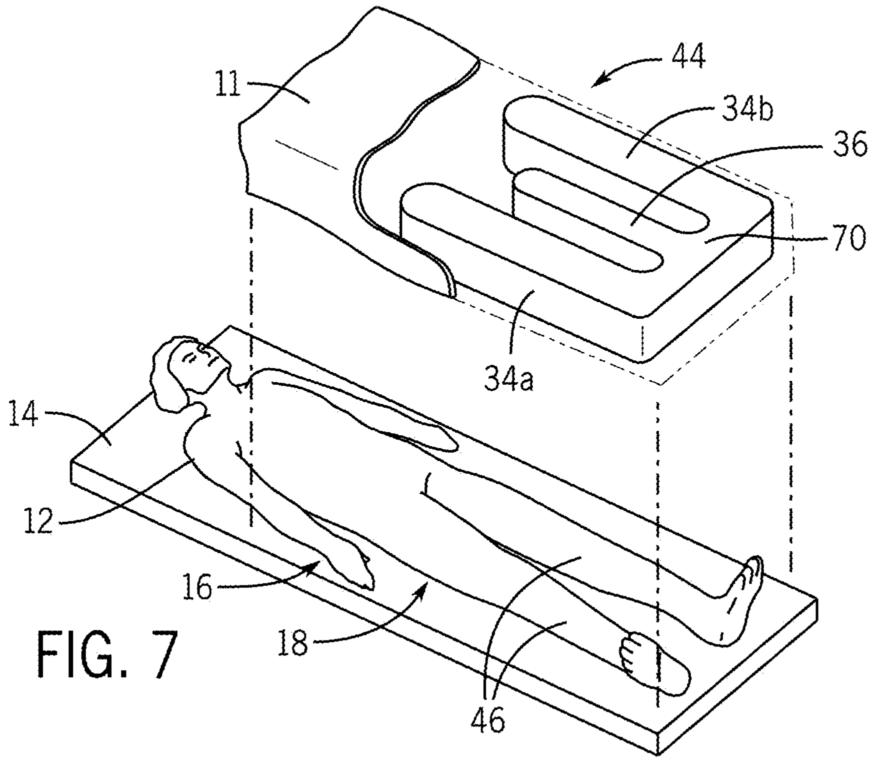
FIG. 7 is a figure similar to FIG. 1 with the trait material in partial cutaway showing an additional inflatable support below the feet.

Referring now to FIG. 7, in one embodiment an inferior inflatable chamber 70 may be provided joining each of the left and right inflatable chambers 34*a* and 34*b* and the central inflatable chamber 36 at their inferior ends to provide additional support to the drape material 11 beyond the feet of the patient 12. Alternatively, the inferior inflatable chamber can adjoin and connect with the two lateral chambers only. The inflatable chamber 70 will generally extend laterally to the lateral outer edges of the inflatable chambers 34*a* and 34*b* and will have a comparable height when inflated to support the surgical drape 10 above the table 14 and to further the slightly concave shape of the upper work surface 44 provided by the surgical drape 10 over the table 14 and extending from the left to the right side of the table 14 as well as toward the patient's feet when the surgical drape 10 is positioned on an average sized patient. As before, this concave work surface 44 may provide improved retention of surgical instruments such as catheters, syringes, and the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What I claim is:

1. A surgical drape comprising:

a sterile sheet sized to cover an area of a patient when lying in a horizontal position on a table, the sheet having left and right edges extending laterally beyond a left and right side of the patient; and a first and second inflatable chamber attached under the left and right edges and sized to elevate the left and right edges above the table when inflated; and further including a third inflatable chamber positioned between the first and second inflatable chambers and sized to be positioned between legs of the patient.

2. The sterile drape of claim 1 wherein the left and right edges extend beyond the first and second inflatable chambers to provide a downwardly extending drape section when positioned on the patient on a radiographic table.

3. The sterile drape of claim 2 wherein the downwardly extending drape section provides an upwardly open pouch.

4. The sterile drape of claim 3 wherein an opening of the pouch is releasably sealable.

5. The sterile drape of claim 1 wherein the sterile sheet provides at least two openings positioned at at least one of a patient groin area and patient wrist area, the openings having releasable covers.

6. The sterile drape of claim 5 wherein the releasable covers are adhesively attached sheets.

7. The sterile drape of claim 1 wherein the first and second inflatable chamber have an inflated height of at least 4 inches between a lower surface adapted to contact the table when inflated and an upper surface defining a height of the left or right edges, respectively.

8. The sterile drape of claim 1 wherein the first and second inflatable chambers hold the sterile sheet to enforce an upwardly concave surface when positioned flanking legs of an average sized patient and inflated.

9. The sterile drape of claim 1 wherein the sterile sheet is sized to cover a superior portion of the patient above a groin region and an inferior portion of the patient below the groin region and the first and second inflatable chambers are limited to the inferior portion.

10. The sterile drape of claim 1 wherein the first, second, and third inflatable chambers include an interconnecting pressure equalization channel.

11. The sterile drape of claim 1 wherein each of the first, second, and third inflatable chambers provides separate inflation valves.

* * * * *